United States Patent
Reddy et al.

(10) Patent No.: US 10,227,305 B2
(45) Date of Patent: Mar. 12, 2019

(54) PROCESS FOR PREPARING INDACATEROL AND SALTS THEREOF

(71) Applicants: G. Pratap Reddy, Telangana (IN); Venkataiah Sunku, Andhra Pradesh (IN); Sunkaraneni Suresh Babu, Andhra Pradesh (IN)

(72) Inventors: G. Pratap Reddy, Telangana (IN); Venkataiah Sunku, Andhra Pradesh (IN); Sunkaraneni Suresh Babu, Andhra Pradesh (IN)

(73) Assignee: G. Pratap Reddy, Telangana (IN)

( * ) Notice: Subject to any disclaimer, the term of this patent is extended or adjusted under 35 U.S.C. 154(b) by 43 days.

(21) Appl. No.: 15/505,760

(22) PCT Filed: Aug. 20, 2015

(86) PCT No.: PCT/IN2015/050095
§ 371 (c)(1),
(2) Date: Feb. 22, 2017

(87) PCT Pub. No.: WO2016/027283
PCT Pub. Date: Feb. 25, 2016

(65) Prior Publication Data
US 2018/0215714 A1   Aug. 2, 2018

(30) Foreign Application Priority Data

Aug. 22, 2014  (IN) .......................... 2698/MUM/2014

(51) Int. Cl.
| C07D 215/227 | (2006.01) |
| C07D 215/26 | (2006.01) |
| C07C 45/46 | (2006.01) |
| C07C 17/16 | (2006.01) |
| C07C 17/354 | (2006.01) |
| C07B 35/02 | (2006.01) |
| C07B 41/06 | (2006.01) |

(52) U.S. Cl.
CPC ............ *C07D 215/26* (2013.01); *C07B 35/02* (2013.01); *C07B 41/06* (2013.01); *C07C 17/16* (2013.01); *C07C 17/354* (2013.01); *C07C 45/46* (2013.01); *Y02P 20/55* (2015.11)

(58) Field of Classification Search
CPC .................................................. C07D 215/227
USPC .......................................................... 546/157
See application file for complete search history.

(56) References Cited

U.S. PATENT DOCUMENTS

| 7,402,598 | B2 * | 7/2008 | Biggadike ............. C07C 311/29 |
| | | | 514/230.5 |
| 7,534,890 | B2 | 5/2009 | Lohse et al. |
| 8,236,959 | B2 * | 8/2012 | Kankan ............... C07D 215/227 |
| | | | 546/157 |
| 2013/0225681 | A1 | 8/2013 | Zacharie et al. |

FOREIGN PATENT DOCUMENTS

| WO | 2004016601 A1 | 2/2004 |
| WO | 2006014704 A1 | 2/2006 |
| WO | 2013132514 A2 | 9/2013 |

OTHER PUBLICATIONS

International Search Report for corresponding International PCT Application PCT/IN2015/050095, dated Mar. 4, 2016.

* cited by examiner

*Primary Examiner* — Charanjit Aulakh
(74) *Attorney, Agent, or Firm* — Workman Nydegger

(57) ABSTRACT

The present invention relates to a process for preparing indacaterol or salts thereof. The process comprises of forming compound of Formula 1 by reacting compound of Formula 2 and compound of Formula 3 in the presence of a solvent to Form compound of Formula 4, which on removal of the protecting groups forms compound of Formula 1.

22 Claims, No Drawings

PROCESS FOR PREPARING INDACATEROL AND SALTS THEREOF

FIELD OF THE INVENTION

The present invention relates to process for preparing beta adrenoceptor agonist, particularly Indacaterol or salts thereof.

BACKGROUND OF THE INVENTION

Indacaterol maleate is a beta-selective adrenoceptor agonist with potent bronchodilator activity. Indacaterol is chemically known as 5-[(R)-2-(5,6-diethyl-indan-2-yl amino)-1-hydroxy-ethyl]-8-hydroxy-(1H)-quinolin-2-one.

U.S. Pat. No. 7,534,890 claims a process to prepare 5-[(R)-2-(5,6-diethyl-indan-2-ylamino)-1-hydroxy-ethyl]-8-hydroxy-(1H)-quinolin-2-one salt. One of the key steps in the process is reacting an epoxide, such as 8-substituted oxy-5-(R)-oxiranyl-(1H)-quinoline-2-one [Formula (I)] with an amine, such as 2-amino-(5,6-diethyl)-indan to form an intermediate 5-[(R)-2-(5,6-diethyl-indan-2-ylamino)-1-hydroxy-ethyl]-8-substituted oxy-(1H)-quinolin-2-one [Formula (IIa)].

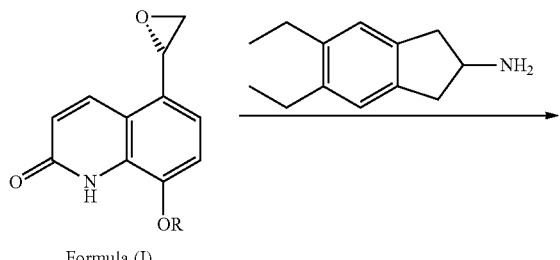

Formula (I)

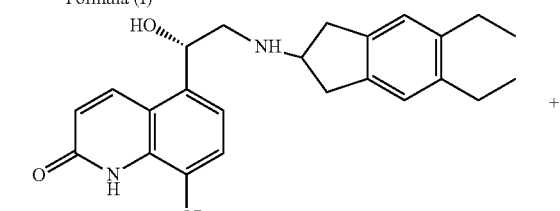

Formula (IIa)

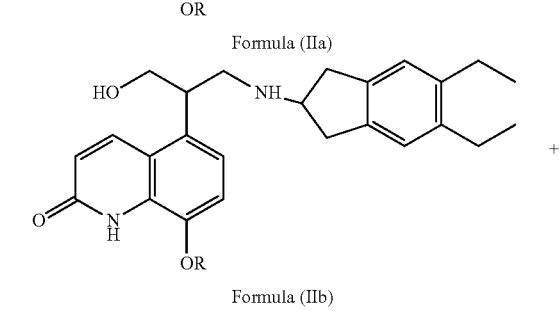

Formula (IIb)

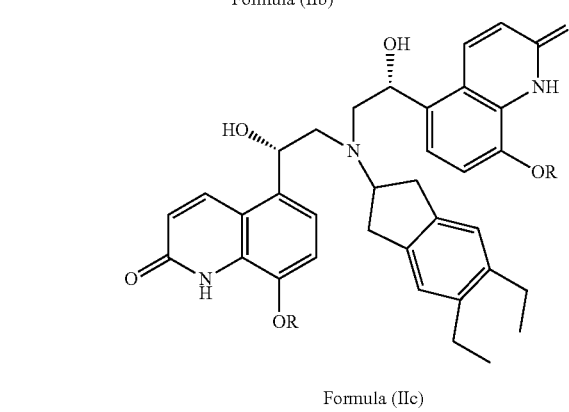

Formula (IIc)

The drawback of this process is opening of epoxide ring is not regioselective and thereby resulting, in formation of substantial quantities of impurities as by products, Formula (IIb) and Formula (IIc) resulting in overall lower yields. The quantity of 2-amino-(5,6-diethyl)-indan used in this step is also large excess than theoretical amounts. Subsequent improvements also did not address this problem effectively.

WO 2013/132514 discloses a process to prepare Indacaterol involving the steps of treating a compound of Formula (III), wherein L is a leaving group, with the amine, 2-amino-(5,6-diethyl)-indan or its acid addition salts to obtain a compound of Formula (IV) or its acid addition salts.

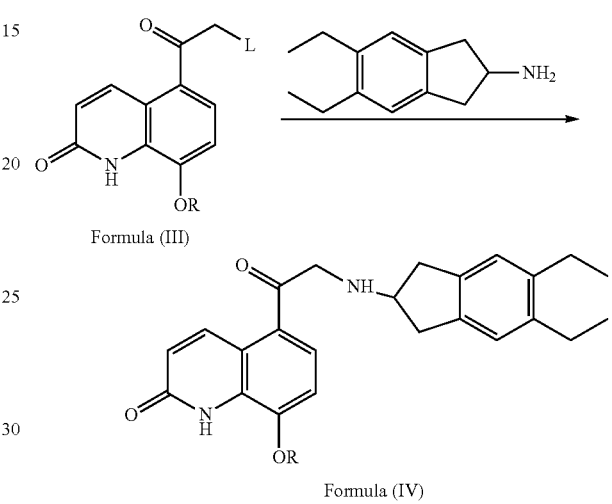

Formula (III)

Formula (IV)

Though higher yields have been claimed, the process has not overcome completely all the problems mentioned earlier.

There is a need for developing a more efficient process for preparing Indacaterol or salts thereof especially for large scale production with higher yields.

SUMMARY OF THE INVENTION

The present invention relates to a process for preparing 5-[(R)-2-(5,6-diethyl-indan-2ylamino)-1-hydroxy-ethyl]-8-hydroxy-(1H)-quinolin-2-one also known as indacaterol. The process comprises of reacting compound of Formula 2 or its acid salt with compound of Formula 3 in the presence of a suitable solvent to form compound of Formula 4. Protecting groups are removed from compound of Formula 4 in the presence of a suitable solvent to form compound of Formula 1.

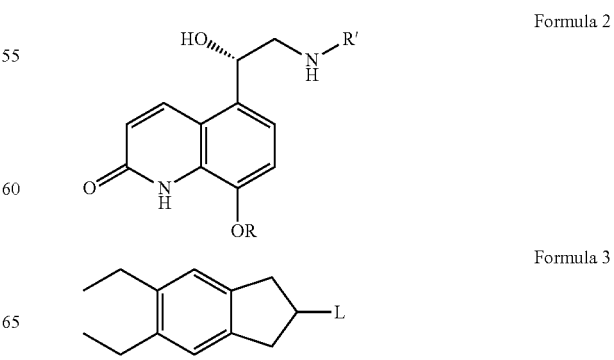

Formula 2

Formula 3

-continued

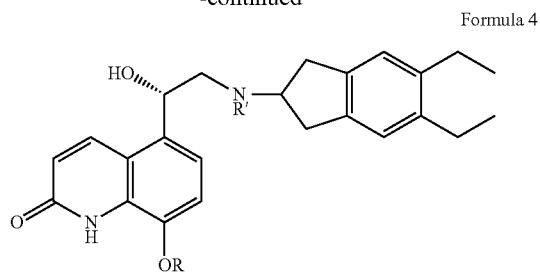

Formula 4

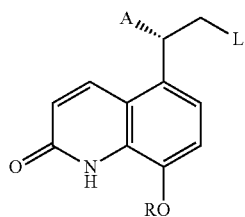

Formula 6

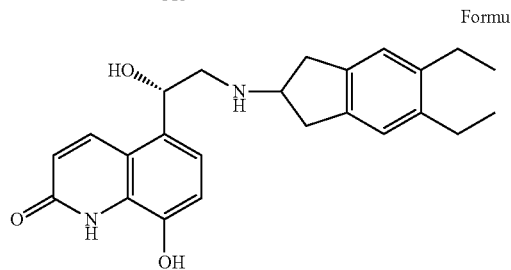

Formula 1 wherein,

L is a leaving group

R is a hydroxy protecting group

R' is H or N-protecting group

The present invention also relates to compound of Formula 2.

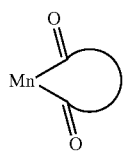

Formula 7

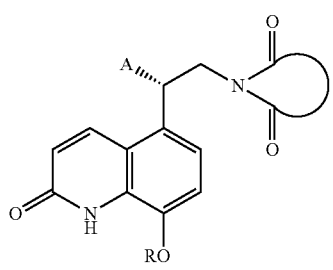

Formula 8

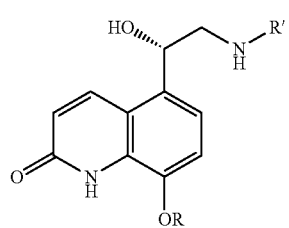

Formula 2

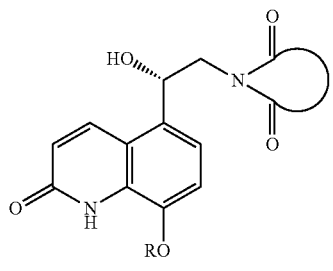

Formula 9

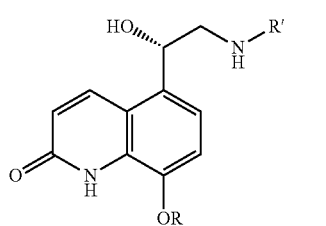

Formula 2 wherein,

R is a hydroxy protecting group

R' is H or N-protecting group

The present invention also relates to a process of preparing compound of Formula 2. The process comprises of reacting compound of Formula 6 with compound of Formula 7 in the presence of a solvent to obtain compound of Formula 8. Compound of Formula 8 is further reacted with a reducing agent in the presence of a catalyst to form compound of Formula 9 followed by treatment with an amine deprotecting agent to obtain compound of Formula 2. Alternatively, compound of Formula 8 can also be treated with an amine deprotecting agent to form compound of Formula 2. Another process of preparing compound of Formula 2 from compound of Formula 6, when L is hydrogen atom, is by treating with an oxidizing agent, reacting with arylalkylamine and reducing to form compound of Formula 2.

wherein,

L is a leaving group

M is H, alkali metal ion

R is a hydroxy protecting group

A is =O, —OH

The present invention also relates to a process for preparing compound of Formula 3, wherein the process comprises of reacting 2-hydroxyindan with a reagent to obtain compound of Formula 10, which is subjected to Freidel-Crafts acylation to form compound of Formula 11, which on reduction gives compound of Formula 12. Compound of Formula 12 is subjected to Freidel-Crafts acylation to form compound of Formula 13, which on reduction forms compound of Formula 3.

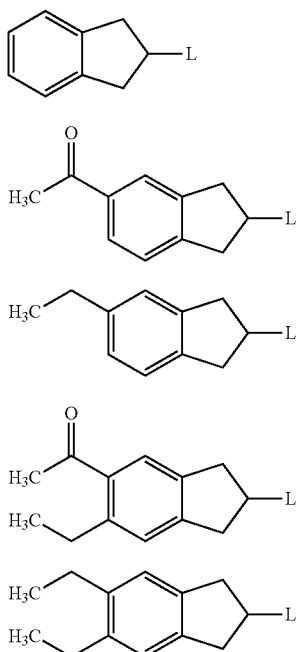

Formula 10

Formula 11

Formula 12

Formula 13

The present invention discloses a process for preparing compound of Formula 4. The process comprises of reacting compound of Formula 2 or its acid salt with compound of Formula 3 in the presence of a solvent to form compound of Formula 4.

Formula 2

Formula 3

Formula 4

DESCRIPTION OF THE INVENTION

An embodiment of the present invention relates to a process for preparing 5-[(R)-2-(5,6-diethyl-indan-2-ylamino)-1-hydroxy-ethyl]-8-hydroxy-(1H)-quinolin-2-one of Formula 1. The process comprises of reacting compound of Formula 2 or its acid salt with compound of Formula 3 in the presence of a solvent to form compound of Formula 4. The temperature of the reaction is maintained in a range of 0° C. to 120° C. Further, the protecting groups of compound of Formula 4 are removed in the presence of a solvent to form 5-[(R)-2-(5,6-diethyl-indan-2-ylamino)-1-hydroxy-ethyl]-8-hydroxy-(1H)-quinolin-2-one of Formula 1. The temperature is maintained in a range of 50-60° C.

Compound of Formula 2 or its acid salt can be treated with compound of Formula 3 optionally in the presence of a base to form compound of Formula 4. An inorganic or organic base is selected from alkali and alkali earth metal carbonate, bicarbonate, hydroxide, hydride, alkoxide, tertiary amines, N-methyl morpholine, diisopropyl ethylamine, N-methyl piperidine, N-methyl pyrrolidione, 1,8-Diazabicyclo[5.4.0]undec-7-ene, 1,4-Diazabicyclo[2.2.2]octane.

Molar equivalents of compound of Formula 3 to compound of Formula 2 are in the ratio of 0.9 to 1.3.

The reaction scheme of preparing compound of Formula 1 is represented below:

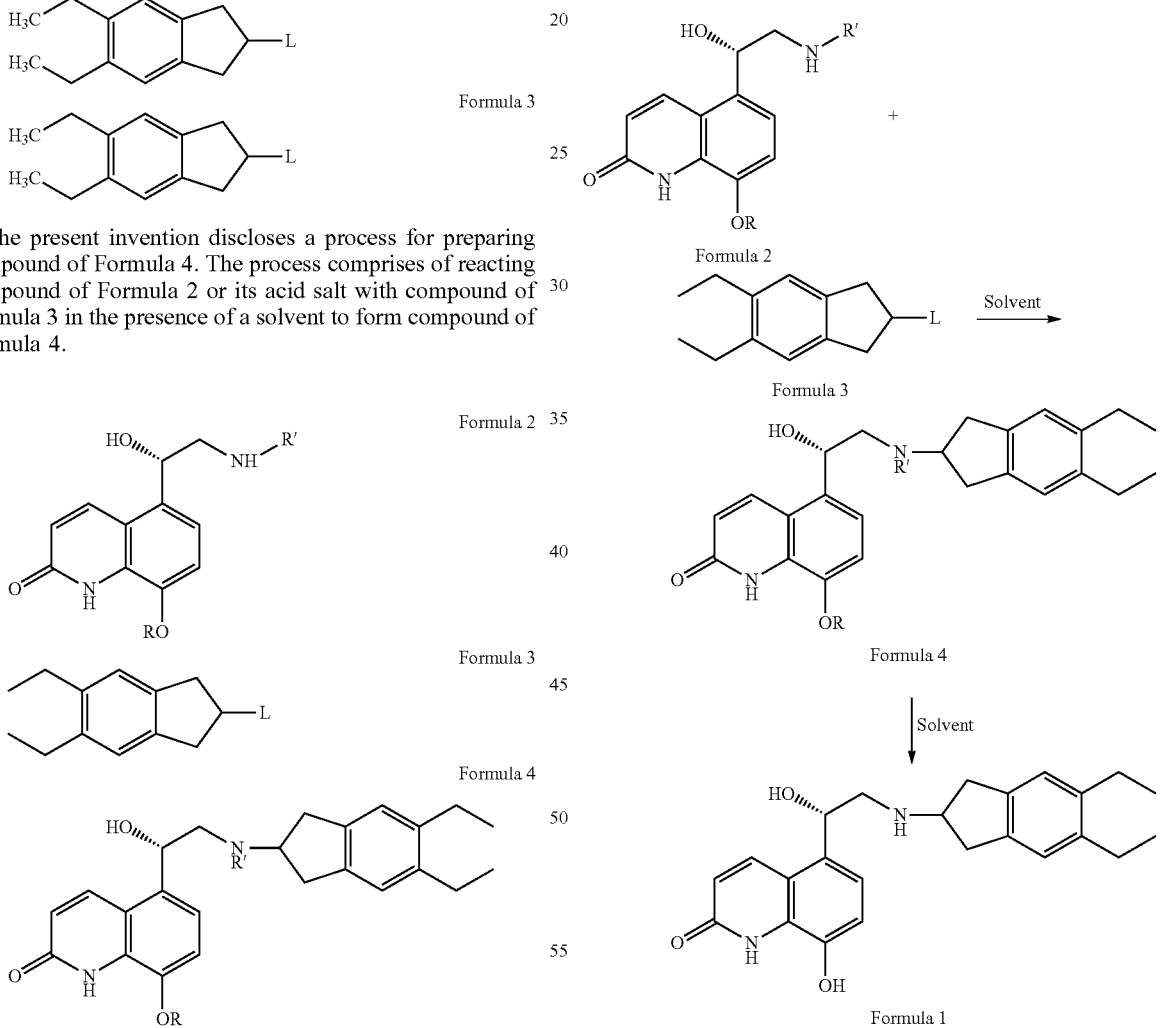

Group L in compound of Formula 3 is a leaving group selected from chloro, bromo, iodo, mesylate, tosylate, alkoxy, aryloxy, acyloxy, silyl derivative, tetrahydropyranyloxy.

Group R in compound of Formula 2 and Formula 4 is a hydroxy protecting group selected from arylalkoxy, alkyl, aryl, alkoxy, alkenyl, cycloalkyl, benzocycloalkyl, arylalkyl, heterocyclic, heteroarylalkyl, haloalkyl and substituted silyl group.

Group R' in compound of Formula 2 and Formula 4 is H or an N-protecting group such as arylalkyl, preferably benzyl.

In a preferred embodiment of the present invention, compound of Formula 1 is treated with an acid in the presence of a solvent to form 5-[(R)-2-(5,6-diethyl-indan-2-ylamino)-1-hydroxy-ethyl]-8-hydroxy-(1H)-quinolin-2-one salt of Formula 5. Temperature is maintained in a range of 0°-70° C.

Acids having $C_2$-$C_4$ carbons such as oxalic acid, tartaric acid, maleic acid, fumaric acid, and succinic acid are used to prepare compound of Formula 5. Inorganic acids such as hydrochloric acid, phosphoric acid, sulfuric acid can also be used.

The solvent is selected from $C_{1-6}$ straight chain or branched alcohols such as methanol, ethanol, isopropanol, tertiary-butyl alcohol, halogenated hydrocarbons such as dichloromethane, ethylene dichloride, chloroform, ketones such as acetone, methyl ethyl ketone, methyl isobutyl ketone, acetonitrile, ethers such as diethyl ether, diisopropyl ether, tetrahydrofuran, methyl tertiary-butyl ether, dioxane, mono- and di-alkyl ethyleneglycol ethers, aprotic solvents such as dimethyl sulfoxide, dimethylformamide, dimethylacetamide or mixtures thereof.

The reaction scheme of preparing compound of Formula 5 from compound of Formula 1 is represented below:

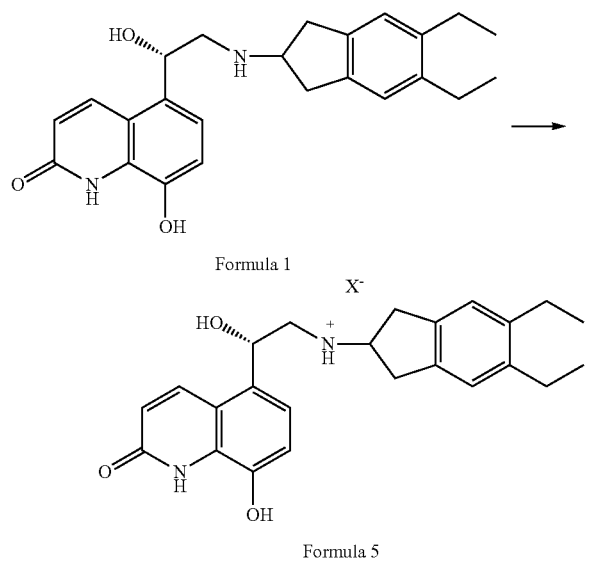

Formula 1

Formula 5 wherein, $X^-$ is an anion, preferably maleate.

Another embodiment of the present invention relates to compound of Formula 2.

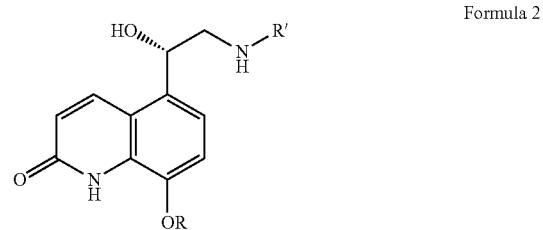

Formula 2 wherein,

R is a hydroxy protecting group selected from arylalkoxy, alkyl, aryl, alkoxy, alkenyl, cycloalkyl, benzocycloalkyl, arylalkyl, heterocyclic, heteroaralkyl, haloalkyl and substituted silyl group.

R' is H or an N-protecting group such as arylalkyl, preferably benzyl.

In a preferred embodiment of the present invention, compound of Formula 2 is

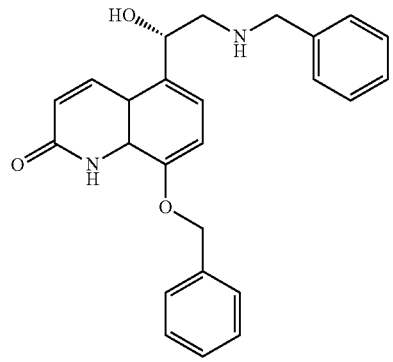 [SMILES: O=C1C=CC2C([C@H](O)CNCc3ccccc3)=CC=C(OCc3ccccc3)C2N1]

An embodiment of the present invention relates to a process for preparing compound of Formula 2. The process comprises of treating compound of Formula 6 with compound of Formula 7 in the presence of a solvent to form compound of Formula 8. The temperature of the reaction is maintained in a range of 0° C. to 120° C. The step of reacting compound of Formula 6 with compound of Formula 7 in the presence of a solvent to form compound of Formula 8 is optionally carried out in the presence of a base. The base is inorganic or organic selected from alkali and alkali earth metal carbonate, bicarbonate, hydroxide, hydride, alkoxide, tertiary amines, N-methyl morpholine, N,N-diisopropyl N-ethylamine, N-methyl piperidine, N-methyl pyrrolidione, 1,8-Diazabicyclo[5.4.0]undec-7-ene, 1,4-Diazabicyclo[2.2.2]octane.

Compound of Formula 7 is a cyclic imide having $C_4$-$C_5$ cycloalkyl ring, cycloalkyl ring fused with aromatic ring with or without substituents, cycloalkyl ring fused with heterocyclic ring with or without substituents, cycloalkenyl group. Preferably, phthalimide or succinimide is used.

The solvent used in the reactions is selected from $C_{1-6}$ straight chain or branched alcohols such as methanol, ethanol, isopropanol, tertiary-butyl alcohol, halogenated hydrocarbons such as dichloromethane, ethylene dichloride, chloroform, ketones such as acetone, methyl ethyl ketone, methyl isobutyl ketone, acetonitrile, ethers such as diethyl ether, diisopropyl ether, tetrahydrofuran, methyl tertiary-butyl ether, dioxane, mono- and di-alkyl ethyleneglycol ethers, aprotic solvents such as dimethyl sulfoxide, dimethylformamide, dimethylacetamide or mixtures thereof.

The reaction scheme for synthesis of compound of Formula 8 is represented below:

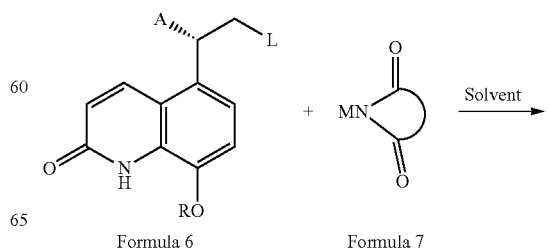

Formula 6    Formula 7

-continued

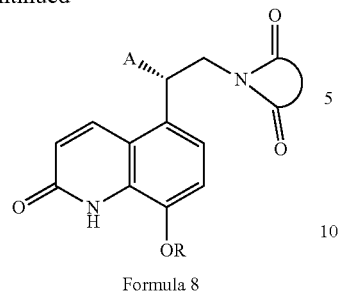

Formula 8

Group L in compound of Formula 6 is a leaving group selected from chloro, bromo, iodo, mesylate, tosylate, silyl derivative, tetrahydropyran.

Group A is hydroxy (—OH) or keto (═O) group.

Group R in compound of Formula 6 and Formula 8 is a hydroxy protecting group selected from arylalkoxy, alkyl, aryl, alkoxy, alkeny groupl, cycloalkyl, benzocycloalkyl, arylalkyl, heterocyclic, heteroarylalkyl, haloalkyl and substituted silyl group.

M is an alkali metal selected from sodium or potassium.

Compound of Formula 2 is prepared via three alternative ways.

Method A:

Compound of Formula 2 is prepared from compound of Formula 8 having A as ═O. Compound of Formula 8 is treated with a reducing agent in the presence of a catalyst to form compound of Formula 9 followed by treatment with an amine deprotecting agent to obtain compound of Formula 2.

The reducing agent is selected from sodium borohydride, borane-tetrahydrofuran complex, borane-dimethyl sulfide complex, borane-diethylaniline complex, diborane along with chiral catalyst selected from (R)-2-methyl-CB S-oxazaborolidine or (1R,2S)-1-amino-2-indanol. The catalyst is selected from borane-THF, borane-DMS, borane-N,N,diethylaniline with chiral catalyst, methyl CBS, phenyl-CBS and 1-amino-2-indanol.

The amine deprotecting agent is selected from hydrazine hydrate or phenyl hydrazine in alcohol, $C_1$-$C_6$ alcohol such as methanol, ethanol, propanol, butanol, pentanol and hexanol, or sodium borohydride.

The reaction scheme of synthesis of compound of Formula 2 by Method A is represented below:

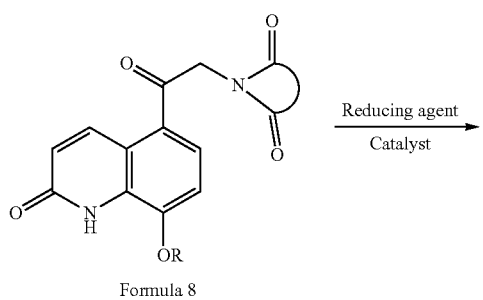

Formula 8 → Reducing agent / Catalyst

-continued

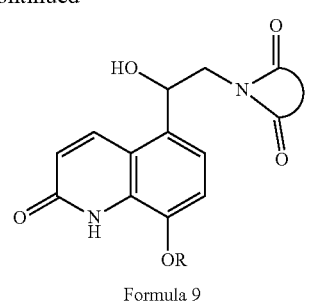

Formula 9

↓ Amine deprotecting agent

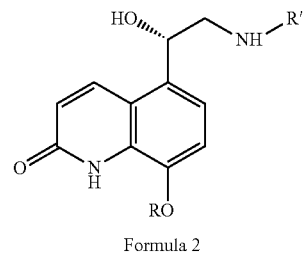

Formula 2

Group R is a hydroxy protecting group selected from arylalkoxy, alkyl, aryl, alkoxy, alkenyl, cycloalkyl, benzocycloalkyl, arylalkyl, heterocyclic, heteroaralkyl, haloalkyl and substituted silyl group.

Group R' is H or N-protecting group such as arylalkyl.

Method B:

Compound of Formula 2 is prepared by compound of Formula 8 having A as —OH. Compound of Formula 8 is treated with an amine deprotecting agent to obtain compound of Formula 2.

The amine deprotecting agent is selected from hydrazine hydrate or phenyl hydrazine in alcohol, $C_1$-$C_6$ alcohol such as methanol, ethanol, propanol, butanol, pentanol and hexanol, or sodium borohydride.

It is a standard method of preparing primary amines by Gabriel method. It is a process, in which, first compound is reacted with hydrazine/phenyl hydrazine or reduced using sodium borohydride and hydrolyzed with acids like hydrochloric or acetic acid.

The reaction scheme of synthesis of compound of Formula 2 by Method B is represented below:

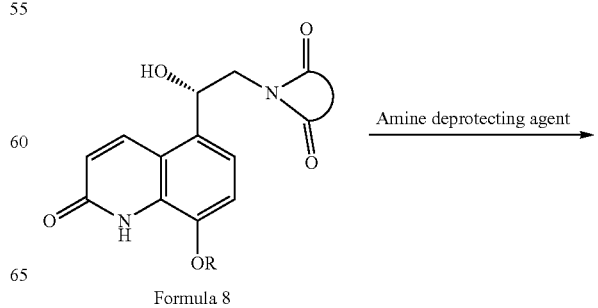

Formula 8 → Amine deprotecting agent

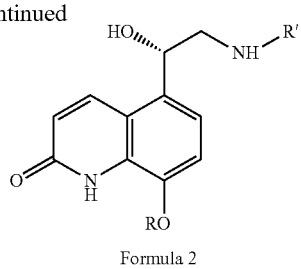

Formula 2

Method C:

Compound of Formula 6, when A is =O, L is H and R is a hydroxy protecting group is treated with an oxidizing agent such as selenium dioxide to form compound of Formula 6a, which on reaction with an arylalkylamine such as benzyl amine gives a keto-imine of Formula 6b. Compound of Formula 6b on reduction with a suitable reducing agent gives compound of Formula 2. Reduction of compound of Formula (6b) with suitable reducing agents can be carried out either in one step to form amino-alcohol (racemic compound) or in two stages by first reducing the imine group to give keto-amine and subsequently reducing the keto group asymmetrically to give compound of Formula 2. In the former case, the racemic amino-alcohol can be resolved into its optically active isomers.

The reducing agent is selected from sodium borohydride, borane-tetrahydrofuran complex, borane-dimethyl sulfide complex, borane-diethylaniline complex, diborane with (R)-2-methyl-CBS-oxazaborolidine or (1R,2S)-1-amino-2-indanol or hydrogenation in presence of Raney-Nickel or noble metals like Palladium, Platinum on charcoal.

A process described in Organic Process Research & Development, 2012, Vol. 16, pp 710-713 can be carried out to prepare compound of Formula 2.

The reaction scheme to synthesize compound of Formula 2 by Method C is as follows:

An embodiment of the present invention relates to a process for preparing compound of Formula 3. The process comprises of treating 2-hydroxyindan with a reagent to form compound of Formula 10. The temperature ranges from 10° C. to 80° C. and the reagent is selected from $SOCl_2$, HBr and HI. Compound of Formula 10 is subjected to Friedel-Crafts acylation to form compound of Formula 11, which on reduction gives compound of Formula 12. Compound of Formula 12 is subjected to Friedel-Crafts acylation to form compound of Formula 13, which on reduction gives compound of Formula 3.

Friedel-Crafts acylation is carried out by known procedures involving solvent selected from nitromethane, methylenedichloride, 1,2-dichloromethane and carbondisulfide; reagents selected from aluminium chloride with acetyl chloride or acetic anhydride. The temperature is maintained in a range of −5° to 30° C.

Compound of Formula 11 and Formula 13 are subjected to reduction using Palladium or Platinum on carbon and hydrogen in acetic acid or a mixture of acetic acid and methanol as solvent at 50° to 60° C. and a pressure of 3 to 4 atmosphere.

The reaction scheme of synthesis of compound of Formula 3 is represented below.

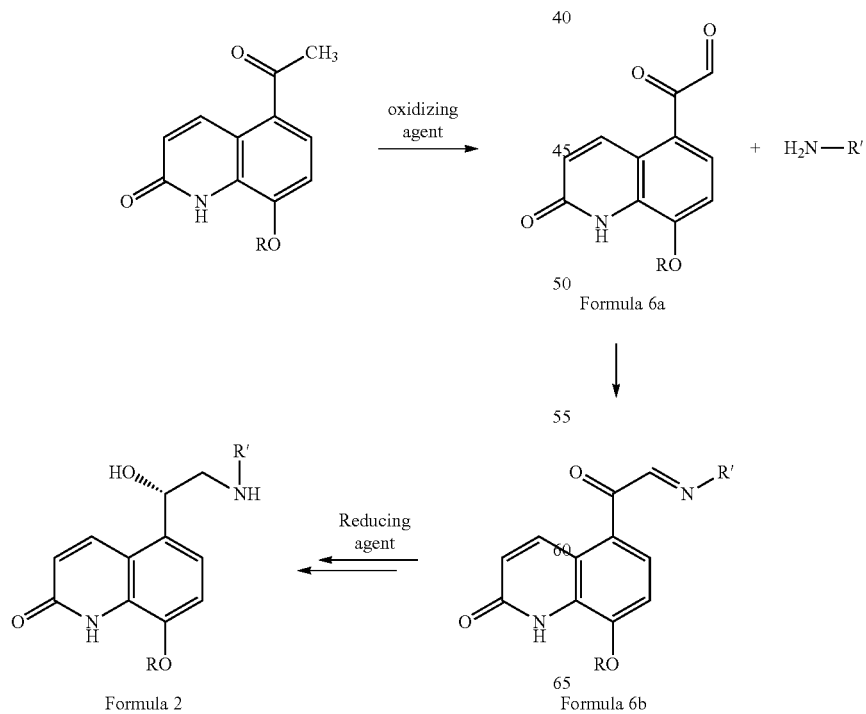

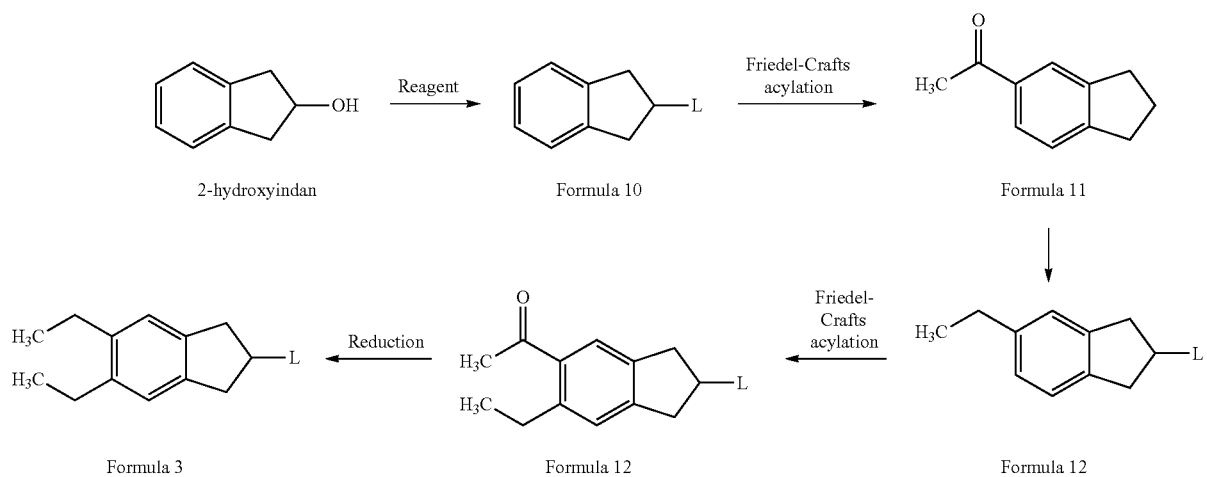

An embodiment of the present invention relates to a process for preparing compound of Formula 4. The process comprises of reacting compound of Formula 2 with compound of Formula 3 in the presence of a solvent to obtain compound of Formula 4 and removing the protecting groups from compound of Formula 4 in the presence of a solvent. The temperature of the reaction is maintained in a range of 0°-120° C.

The process of the present invention results in the formation of products in high yield without the formation of any side products. The purity of the products is improved, thus additional purification steps are avoided. The process is economically viable and the intermediates such as compound of Formula 2 can be used to make other drugs.

EXAMPLES

The following examples illustrate the invention, but are not limiting thereof.

Example 1

Process to Prepare 5-[(R)-2-(5,6-diethyl-indan-2-ylamino)-1-hydroxy-ethyl]-8-hydroxy-(1H)-quinolin-2-one 2-Chloro-5,6-diethylindan (4.2 g) was added to a solution of 5-[(R)-(2-amino-1-hydroxy-ethyl)-8-phenylmethoxy-(1H)-quinolin-2-one (6 g) in dimethylformamide (20 ml) followed by addition of N,N-diisopropyl-N-ethylamine (3.6 g) and sodium iodide (1 g) at room temperature and stirred for 10 minutes. The reaction mixture was heated to 90° C. and the temperature was maintained at 90° C. till the completion of reaction. The reaction mass was cooled to room temperature and diluted with dichloromethane (100 ml) and water (100 ml) and stirred for 30 minutes. The organic phase was separated and the aqueous layer was extracted with dichloromethane. Combined organic layer was washed with water, dried and concentrated. The resulting residue was dissolved in isopropyl alcohol under reflux and cooled slowly to obtain 5-[(R)-2-(5,6-diethyl-indan-2-ylamino)-1-hydroxy-ethyl]-8-phenylmethoxy-(1H)-quinolin-2-one, which was isolated by filtration and dried under vacuum (7.4 g). Yield: 79.3%. Purity of the product is >95% (HPLC).

Example 2

Process to Prepare 5-[(R)-2-(5,6-diethyl-indan-2-ylamino)-1-hydroxy-ethyl]-8-hydroxy-(1H)-quinolin-2-one Solution of 5-[(R)-2-(5,6-diethyl-indan-2-ylamino)-1-hydroxy-ethyl]-8-phenylmethoxy-(1H)-quinolin-2-one (10 g) in methanol (100 ml) and acetic acid (20 ml) was hydrogenated using palladium on charcoal 5% (1.5 g) until completion of the reaction. The mixture was filtered over celite and the filtrate was concentrated at 55° C. under vacuum. The residue obtained was dissolved in hot methanol to precipitate 5-[(R)-2-(5,6-diethyl-indan-2-ylamino)-1-hydroxy-ethyl]-8-hydroxy-(1H)-quinolin-2-one.

Example 3

Process to Prepare 5-[(R)-2-(5,6-diethyl-indan-2-ylamino)-1-hydroxy-ethyl]-8-hydroxy-(1H)-quinolin-2-one maleate Crude 5-[(R)-2-(5,6-diethyl-indan-2-ylamino)-1-hydroxy-ethyl]-8-hydroxy-(1H)-quinolin-2-one prepared by the process of Example 2 was added to a solution of maleic acid (2.6 g) in methanol and the resulting clear solution was slowly cooled to 5° C. and stirred for 2 hours at the same temperature. The slurry was filtered, washed with cold methanol and dried to obtain 5-[(R)-2-(5,6-diethyl-indan-2-ylamino)-1-hydroxy-ethyl]-8-hydroxy-(1H)-quinolin-2-one maleate (8.8 g). Yield: 83.5%. Purity of the product is >99%. E.e. >99%.

Example 4

Process for Preparing 5-[(R)-(2-phthalimido-1-hydroxy-ethyl)-8-phenylmethoxy-(1H)-quinolin-2-one Diisopropylethylamine (6 g) was added to a solution of phthalimide (6 g) in dimethylformamide (30 ml) at room temperature. To this solution, 8-(phenylmethoxy)-5-[(R)-2-bromo-1-hydroxy-ethyl]-(1H)-quinoline-2-one (11 gm) was added slowly followed by sodium iodide (1 g). The resulting mass was heated to 90° C. and stirred till the completion of reaction as monitored by TLC. The reaction mass was diluted with water (200 ml) and the crude product was isolated by filtration. The wet filter cake was suspended in water (60 ml), stirred for 1 hour, filtered, washed with water to obtain 5-[(R)-(2-phthalimido-1-hydroxy-ethyl)-8-phenyl-methoxy-(1H)-quinolin-2-one (10.4 gm) after drying. Yield: 80.7%.

Method A—Process for Preparing 5-[(R)-(2-amino-1-hydroxy-ethyl)-8-phenylmethoxy-(1H)-quinolin-2-one To a solution of 5-[(R)-(2-phthalimido-1-hydroxy-ethyl)-8-phenylmethoxy-(1H)-quinolin-2-one (13.2 g) in a mixture of isopropanol (86 ml) and water (14 ml) sodium borohydride (4.6 g) was added slowly at room temperature and stirred overnight. Thereafter, the pH of the reaction mass was lowered to 5.5 with acetic acid, and then the reaction mass was heated to reflux for two hours. Isopropanol was distilled out under reduced pressure. The residue was diluted with ethyl acetate (120 ml) and concentrated hydrochloric acid (8 ml) was added and stirred for 15 minutes for the salts to precipitate out. The reaction mass was filtered and the salt was washed with ethyl acetate. To the clear filtrate concentrated hydrochloric acid (10 ml) was added and stirred at 5° C. for 30 minutes for 5-[(R)-(2-amino-1-hydroxy-ethyl)-8-phenylmethoxy-(1H)-quinolin-2-one to separate out as hydrochloride salt. The product was isolated by filtration and dried under vacuum (8.2 g). The hydrochloride salt was dissolved in minimum amount of water and basified with sodium hydroxide solution. The product was isolated as free amine by concentrating the solution under reduced pressure and extracting the residue with isopropyl alcohol and distilling out the solvent (7.45 g). Yield 80%.

1H-NMR (CDCl3) ppm: 2.56-2.70 (m, 2H), 3.35 (s, br, 2H, exchangeable), 4.89 (m, 1H), 5.29 (s, 2H), 5.76 (s, 1H, exchangeable), 6.53 (d, 1H), 7.11-7.19 (dd, 2H), 7.29-7.36 (dd, 1H), 7.39 (d, 2H), 7.57 (d, 2H), 8.21 (d, 1H), 10.7 (s, br, 1H, exchangeable).

Method B—Process for preparing 5-[(R)-(2-amino-1-hydroxy-ethyl)-8-phenylmethoxy-(1H)-quinolin-2-one To a solution of 5-[(R)-(2-phthalimido-1-hydroxy-ethyl)-8-phenylmethoxy-(1H)-quinolin-2-one (10 g) in ethanol (60 ml) hydrazine hydrate (4.8 g) was added and refluxed the mixture for about 6 hours. The solvent was distilled out under reduced pressure. To the residue, concentrated hydrochloric acid (16 ml) was added and heated to about 80° C. and maintained till the completion of the reaction. The reaction mass was cooled to room temperature and filtered. The clear filtrate was basified and concentrated under reduced pressure. The product was isolated as free amine (5.8 g) by extracting with isopropyl alcohol and distilling out the solvent. Yield: 83%.

Method C Preparation of 5-(2-benzylamino-1-hydroxy-ethyl)-8-phenylmethoxy-(1H)-quinolin-2-one 5-Acetyl-8-phenylmethoxy-(1H)-quinolin-2-one (30 g) was refluxed with selenium dioxide (11.5 g) in a mixture of dioxane (350 ml) and water (30 ml) for 16 hours. The reaction mixture was diluted with dioxane (150 ml) and precipitated inorganic salts were removed by filtration. Clear filtrate was concentrated to about 60 ml under vacuum and diluted with methanol (100 ml). The reaction mass was cooled to 15° C. and benzylamine (7.5 g) was added slowly over a period of 45 minutes and stirred at the same temperature for two hours. The reaction mass was further cooled to 0° C. and sodium borohydride (2.8 g) was added slowly over a period of one hour. Thereafter, the reaction mass was stirred at room temperature for 12 hours. The reaction mixture was concentrated under vacuum and diluted with 300 ml water and stirred at 20° C. for three hours. The precipitated product was collected by filtration, washed with water followed by isopropyl ether and then dried (28.2 g) to obtain 5-(2-benzylamino-1-hydroxy-ethyl)-8-phenyl-methoxy-(1H)-quinolin-2-one.

Example 5

Preparation of 5-acetyl-8-phenylmethoxy-(1H)-quinolin-2-one

To a solution of 5-acetyl-8-hydroxy-(1H)-quinolin-2-one (35 g) in dimethylformamide (175 ml) potassium carbonate (35 g) was added at room temperature and stirred for 10 minutes. To the suspension, benzylbromide (32 g) was slowly added over a period of 30 minutes and stirred for 2 hours at the same temperature for completion of reaction (monitored by TLC). The reaction mass was diluted with water (800 ml) and stirred for 20 minutes for the product to precipitate out. The product was filtered, washed with water and dried under vacuum to get the title product (48 g).

Example 6

Preparation of 5-(2-bromoacetyl)-8-phenylmethoxy-(1H)-quinolin-2-one

Boron trifluoride-diethyletherate (29 ml) was slowly added to a solution of 5-acetyl-8-phenylmethoxy-(1H)-quinolin-2-one (50 g) in dichloromethane (500 ml) at 0° C. and stirred for 10 minutes at the same temperature to get a thick precipitate. The reaction mass was heated to reflux temperature and bromine solution was added (29 g in 190 ml dichloromethane) slowly over a period of 2 hours under reflux (the HBr fumes coming from the condenser was scrubbed). Thereafter, the reaction mass was refluxed for further 45 minutes. The solvent was distilled out completely under vacuum and the mass was triturated with 10% aqueous sodium carbonate solution (100 ml). The suspension was filtered, washed with water and the crude product was taken for the next stage reaction.

Example 7

Preparation of 5-(2-phthalimido-1-oxo-ethyl)-8-phenylmethoxy-(1H)-quinolin-2-one Potassium carbonate (33.4 g) was added to a solution of phthalimide (21.73 g) in dimethylformamide (80 ml) at room temperature and stirred for 10 minutes. To this suspension, crude 5-(2-bromoacetyl)-8-phenylmethoxy-(1H)-quinolin-2-one of example 6, dissolved in dimethylformamide (120 ml), was added slowly over a period of 20 minutes. The resulting suspension was stirred at 50° C. for about 1 hour for the completion of reaction as monitored by TLC. The mixture was diluted with water (800 ml) and the crude product was isolated by filtration. The wet filter cake was suspended in water (600 ml), stirred for 1 hour, filtered, washed with water and dried under vacuum to get 5-(2-phthalimido-1-oxo-ethyl)-8-phenylmethoxy-(1H)-quinolin-2-one (67.4 g). Over all yield (after two steps): 90%.

Example 8

Preparation of 5-[(R)-(2-phthalimido-1-hydroxy-ethyl)-8-phenylmethoxy-(1H)-quinolin-2-one To a solution of (R)-2-methyl-CBS-oxazaborolidine (1M in toluene, 4.2 ml) in dry tetrahydrofuran (THF, 50 ml) Borane-diethylaniline (19 ml) was added slowly at −10° C. and the contents were stirred at the same temperature for 15 minutes. A solution of 5-(2-Phthalimido-1-oxo-ethyl)-8-phenylmethoxy-(1H)-quinolin-2-one (8.3 g), of example 7, in a mixture of dry THF (50 ml) and dichloromethane (50 ml), was added slowly to the reaction mass at −10° C. The reaction mass was further stirred for 2 hours and then methanol was added and the temperature was slowly raised to room temperature. Dilute sulfuric acid (6N, 10 ml) was added to the reaction mixture and stirred for 15 minutes. The reaction mixture was concentrated under vacuum and the crude mass was extracted with ethyl acetate. The organic phase was washed with dilute sulfuric acid and then water. The solvent was distilled out completely under vacuum and triturated with hexane. The compound was isolated by filtration and dried (7.6 g). Yield: 91.1%. e.e. >97%.

Example 9

Process of Preparing 2-chloroindan 2-hydroxy indan (100 g) was dissolved in 1,2-dichloroethane (400 ml) and added to thionyl chloride (125 g) slowly over a period of an hour. Temperature was maintained at less than 10° C. Thereafter, the reaction mass was slowly heated and refluxed till the completion of the reaction. The reaction was monitored by TLC. The reaction mass was cooled to room temperature and poured in to ice water, stirred for 1 hour and organic layer was separated. The aqueous layer was extracted with dichloroethane. Organic layers were combined and washed with water, sodium bicarbonate solution and dried over anhydrous sodium sulphate. Solvent was distilled out completely and the crude product was distilled under vacuum to obtain 2-chloroindan as a colorless liquid (118 g).

Example 10

Process for Preparing 5-acetyl-2-chloroindan

Aluminium chloride (146 g) was added in small lots to nitromethane (500 ml) and the solution was cooled to 5° C. under inert atmosphere while stirring. Acetyl chloride (84 g) was slowly added keeping the temperature at 5° C. Solution of 2-chloroindan (118 g) was slowly added in acetyl chloride (84 g) keeping temperature at 5° C. After completion of reaction, monitored by TLC, the reaction mass was poured into cold 1N HCl (2000 ml) solution and stirred for 30 minutes. The product was extracted into di-isopropyl ether. The combined organic layer was washed with water, bicarbonate solution, brine and dried over anhydrous sodium sulphate. The solvent was completely distilled out to obtain 5-acetyl-2-chloroindan as yellow waxy solid (130 g).

Example 11

Process for Preparing 2-chloro-5-ethylindan

1 Liter hydrogenation vessel was charged with 50 grams of 5-acetyl-2-chloroindan, 400 ml of methanol and 10 ml of acetic acid. Palladium on charcoal 5% (5 g) was added and the reaction mass was hydrogenated until complete conversion to 2-chloro-5-ethylindan. The mixture was filtered over a bed of celite. The filtrate was concentrated under reduced pressure to obtain 2-chloro-5-ethylindan as an oily mass (42 g).

Example 12

Process for Preparing 5-acetyl-2-chloro-6-ethylindan 5-acetyl-2-chloro-6-ethylindan was prepared from 2-chloro-5-ethylindan (20 g) in accordance with the procedure followed in Example 10.

Example 13

Process for Preparing 2-chloro-5,6-diethylindan

Hydrogenation of 5-acetyl-2-chloro-6-ethylindan using Palladium on charcoal adopting the procedure as reported in Example 11, gave 2-chloro-5,6-diethylindan as a liquid. The crude product was distilled under vacuum to get colorless liquid.
1H-NMR (CDCl3) ppm: 1.19-1.29 (t, 6H), 2.61-2.66 (q, 4H), 3.13-3.18 (dd, 2H), 3.36-3.41 (dd, 2H), 4.66-4.72 (m, 1H), 7.05 (s, 2H).

The invention claimed is:
1. A process for preparing 5-[(R)-2-(5,6-diethyl-indan-2-ylamino)-1-hydroxy-ethyl]-8-hydroxy-(1H)-quinolin-2-one of Formula 1, the process comprising:
  (i) reacting compound of Formula 2 or its acid salt with compound of Formula 3 in the presence of a solvent to form compound of Formula 4; and

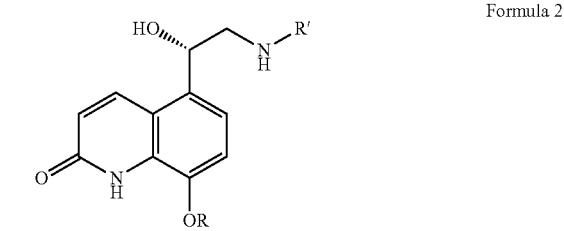

Formula 2

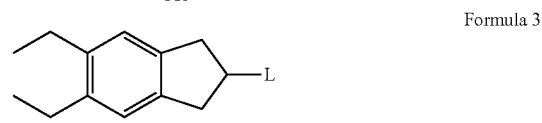

Formula 3

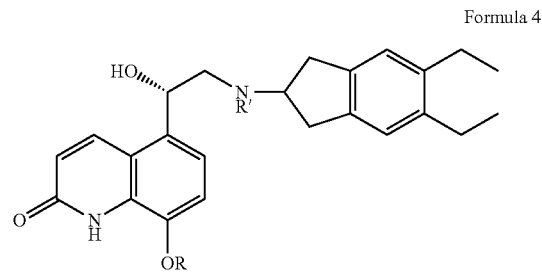

Formula 4 wherein,
L is a leaving group
R is a hydroxy protecting group
R' is H or an N-protecting group (ii) removing the protecting groups from compound of Formula 4 in the presence of a solvent to form compound of Formula 1;

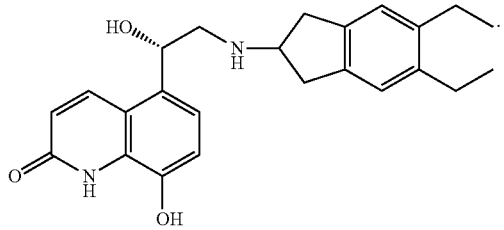

Formula 1

2. The process as claimed in claim 1 comprising treating compound of Formula 1 with an acid in the presence of a solvent to form 5-[(R)-2-(5,6-diethyl-indan-2-ylamino)-1-hydroxy-ethyl]-8-hydroxy-(1H)-quinolin-2-one salt of Formula 5;

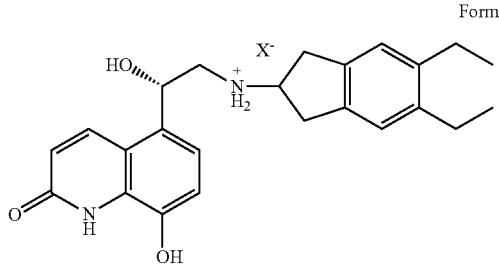

Formula 5 wherein, X⁻ is an anion.

3. The process as claimed in claim 1 wherein step (i) is carried out in the presence of a base.

4. The process as claimed in claim 2, wherein acid is selected from acids such as oxalic acid, tartaric acid, maleic acid, fumaric acid, succinic acid, hydrochloric acid, phosphoric acid, sulfuric acid.

5. The process of preparing compound of Formula 2 as claimed in claim 1, the process comprising
(i) reacting compound of Formula 6 with compound of Formula 7 in the presence of a solvent to obtain compound of Formula 8; and

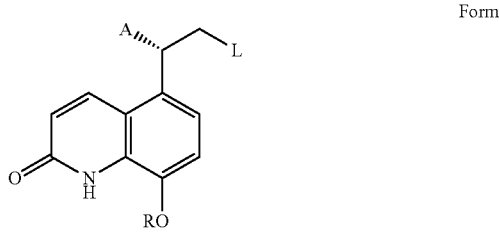

Formula 6

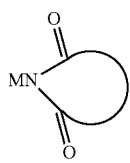

Formula 7

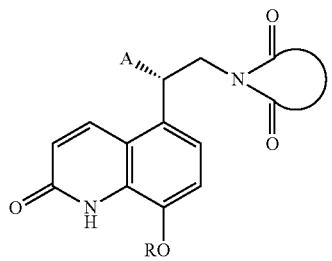

Formula 8 wherein,
L is a leaving group
M is H, alkali metal ion
R is a hydroxy protecting group
A is =O, —OH
(ii) reacting compound of Formula 8, when A is =O with a reducing agent in the presence of a catalyst to form compound of Formula 9 followed by treatment with an amine deprotecting agent to obtain compound of Formula 2; or

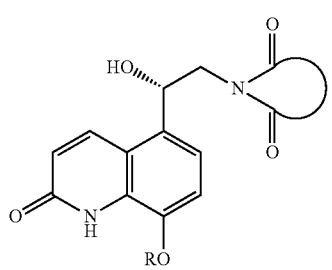

Formula 9

Formula 2

(ii) treating compound of Formula 8, when A is —OH with an amine deprotecting agent to obtain compound of Formula 2; or

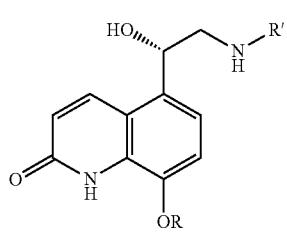

Formula 2 wherein, R is hydroxy protecting group
R' is H or an N-protecting group
(iii) treating compound of Formula 6, when A is =O and L is H with an oxidizing agent, reacting with an arylalkylamine and reducing to form compound of Formula 2.

6. The process as claimed in claim 5, wherein the catalyst is selected from sodium borohydride, borane-THF, borane-DMS, borane-N,N,diethylaniline with chiral catalyst, methyl-CBS, phenyl-CBS and 1-amino-2-indanol or hydrogenation in presence of Raney-Nickel or noble metals like Palladium, Platinum on charcoal.

7. The process as claimed in claim 1, wherein the hydroxy protecting group R is selected from arylalkoxy, alkyl, aryl, alkoxy, alkenyl, cycloalkyl, benzocycloalkyl, aralkyl, heterocyclic, heteroaralkyl, haloalkyl, and a substituted silyl group.

8. The process as claimed in claim 1, wherein L is selected from chloro, bromo, iodo, mesylate, tosylate, alkyloxy, aryloxy, acyloxy, silyloxy derivative, tetrahydropyranyloxy, hydrogen.

9. The process as claimed in claim 5, wherein compound of Formula 7 is a cyclic imide having $C_4$-$C_5$ cycloalkyl ring, cycloalkyl ring fused with aromatic ring with or without substituents, cycloalkyl ring fused with heterocyclic ring with or without substituents, cycloalkenyl group.

10. The process as claimed in claim 5, wherein M in Formula 7 is an alkali metal selected from sodium or potassium.

11. The process as claimed in claim 3, wherein the base is inorganic or organic selected from alkali and alkali earth metal carbonate, bicarbonate, hydroxide, hydride, alkoxide, tertiary amines, N-methyl morpholine, N,N diisopropyl N-ethylamine, N-methyl piperidine, N-methyl pyrrolidine, 1,8-Diazabicyclo[5.4.0]undec-7-ene, 1,4-Diazabicyclo[2.2.2]octane.

12. The process as claimed in claim 1, wherein the solvent is selected from $C_{1-6}$ straight chain or branched alcohols, halogenated hydrocarbons, ketones, ethers such as diethyl ether, diisopropyl ether, tetrahydrofuran, methyl tertiary-butyl ether, dioxane, mono- and di-alkyl ethyleneglycol ethers, aprotic solvents or mixtures thereof.

13. The process as claimed in claim 1, wherein the temperature in step (i) is maintained in the range of 0° C. to 120° C.

14. The process as claimed in claim 5, wherein the reducing agent is selected from sodium borohydride, borane-tetrahydrofuran complex, borane-dimethyl sulfide complex borane-diethylaniline complex, diborane along with chiral catalyst selected from (R)-2-methyl-CBS-oxazaborolidine or (1R,2S)-1-amino-2-indanol or hydrogenation in presence of Raney-Nickel or noble metals like Palladium, Platinum on charcoal, oxidizing agent is selenium dioxide and arylalkylamine is benzylamine.

15. The process as claimed in claim 5, wherein the amine deprotecting agent is hydrazine hydrate or phenyl hydrazine in an alcohol, $C_1$-$C_6$ alcohol sodium borohydride.

16. The process for preparing compound of Formula 3 as claimed in claim 1, the process comprising
(i) treating 2-hydroxyindan with a reagent to form compound of Formula 10;

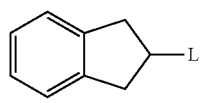

Formula 10

(ii) subjecting compound of Formula 10 to Friedel-Crafts acylation to form compound of Formula 11;

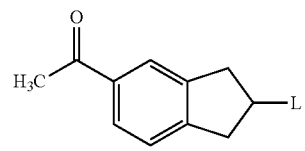

Formula 11

(iii) subjecting compound of Formula 11 to reduction to obtain compound of Formula 12;

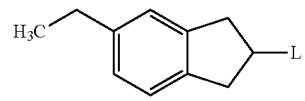

Formula 12

(iv) subjecting compound of Formula 12 to Friedel-Crafts acylation to form compound of Formula 13; and

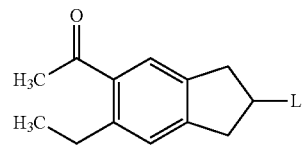

Formula 13

(v) subjecting compound of Formula 13 to reduction to obtain compound of Formula 3

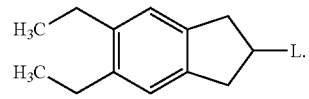

Formula 3

17. The process as claimed in claim 16, wherein the leaving group L is selected from chloro, bromo, iodo, mesylate, tosylate, alkyloxy, aryloxy, acyloxy, silyloxy derivative, tetrahydropyranyloxy.

18. The process as claimed in claim 16, wherein the reagent is selected from $SOCl_2$, HBr and HI or any other suitable reagent depending on the group L.

19. A compound of Formula 2

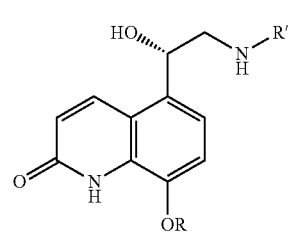

Formula 2 wherein,
R is a hydroxy protecting group
R' is H.

20. The compound as claimed in claim 19, wherein the hydroxy protecting group R is selected from the group consisting of arylalkoxy, alkyl, aryl, alkoxy, alkenyl, cycloalkyl, benzocycloalkyl, aralkyl, heterocyclic, heteroaralkyl, haloalkyl, and a substituted silyl group.

21. A process for preparing compound of Formula 4 as claimed in claim 1, the process comprising:

(i) reacting compound of Formula 2 or its acid salt with compound of Formula 3 in the presence of a solvent to form compound of Formula 4

(ii) removing the protecting groups from compound of Formula 4 in the presence of a solvent to form compound of Formula 1;

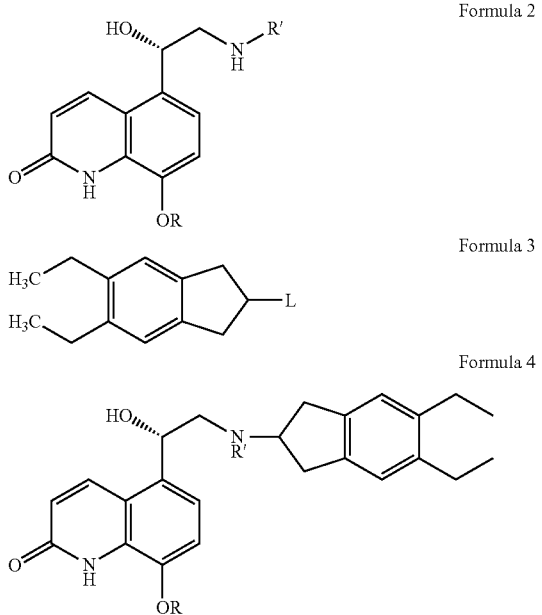

Formula 2

Formula 3

Formula 4

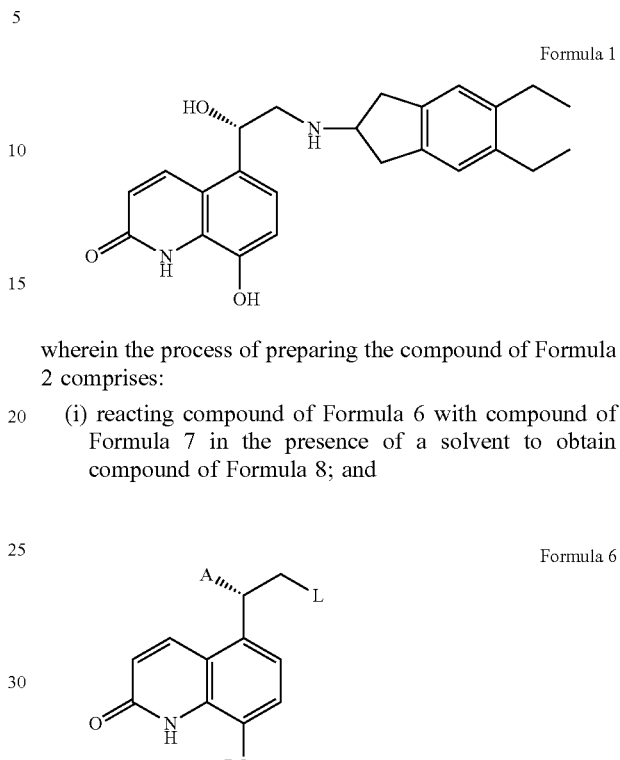

Formula 1 wherein the process of preparing the compound of Formula 2 comprises:

(i) reacting compound of Formula 6 with compound of Formula 7 in the presence of a solvent to obtain compound of Formula 8; and Formula 6

Formula 7

Formula 8 wherein,
L is a leaving group
R is a hydroxy protecting group
R' is H or N-protecting group.

22. A process for preparing 5-[(R)-2-(5,6-diethyl-indan-2-ylamino)-1-hydroxy-ethyl]-8-hydroxy-(1H)-quinolin-2-one of Formula 1, the process comprising:

(i) reacting compound of Formula 2 or its acid salt with compound of Formula 3 in the presence of a solvent to form compound of Formula 4; and

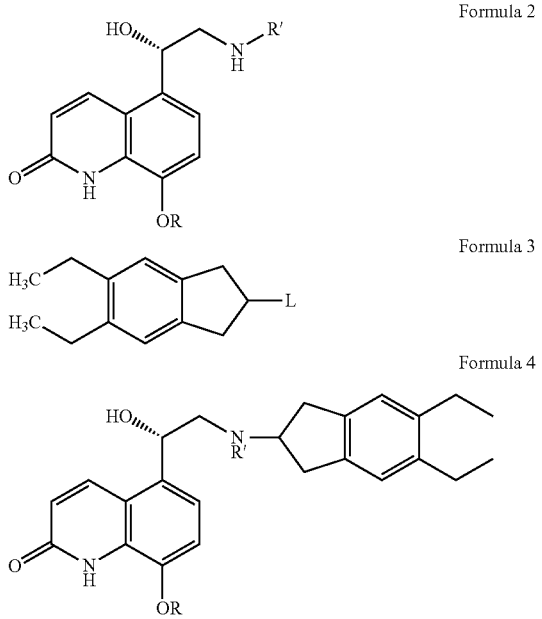

Formula 2

Formula 3

Formula 4 wherein,
L is a leaving group
R is a hydroxy protecting group
R' is H or an N-protecting group wherein,
L is a leaving group
M is H, alkali metal ion
R is a hydroxy protecting group
A is =O, —OH (ii) reacting compound of Formula 8, when A is =O with a reducing agent in the presence of a catalyst to form compound of Formula 9 followed by treatment with an amine deprotecting agent to obtain compound of Formula 2; or

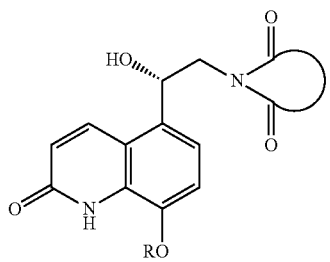

Formula 9

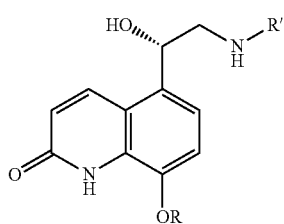

Formula 2

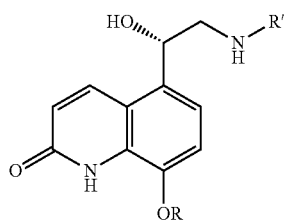

Formula 2

(ii) treating compound of Formula 8, when A is —OH with an amine deprotecting agent to obtain compound of Formula 2; or wherein, R is hydroxy protecting group R' is H or an N-protecting group (iii) treating compound of Formula 6, when A is =O and L is H with an oxidizing agent, reacting with an arylalkylamine and reducing to form compound of Formula 2;

wherein the amine deprotecting agent is hydrazine hydrate or phenyl hydrazine in an alcohol, $C_1$-$C_6$ alcohol water, ethers and sodium borohydride.

\* \* \* \* \*